United States Patent [19]

Tikkanen

[11] Patent Number: 5,032,388

[45] Date of Patent: Jul. 16, 1991

[54] METHOD OF PREVENTING TARTAR FORMATION

[75] Inventor: Matti H. A. Tikkanen, Espoo, Finland

[73] Assignees: Kaj Rainer Lilius; Matti Haakon August Tikkanen, both of Finland

[21] Appl. No.: 246,287

[22] Filed: Sep. 19, 1988

Related U.S. Application Data

[63] Continuation of Ser. No. 896,801, Aug. 15, 1986, abandoned, which is a continuation of Ser. No. 806,742, Dec. 9, 1985, abandoned.

[30] Foreign Application Priority Data

Dec. 18, 1984 [FI] Finland ................................. 845004

[51] Int. Cl.[5] ......................... A61K 7/16; A61K 7/22; A61K 7/24

[52] U.S. Cl. ........................................ 424/49; 424/54; 424/55; 514/899; 514/901

[58] Field of Search ............................. 424/49, 54, 55; 514/899, 901

[56] References Cited

U.S. PATENT DOCUMENTS

| | | | |
|---|---|---|---|
| 3,988,434 | 10/1976 | Schole et al. | 424/54 |
| 4,130,638 | 12/1978 | Dhabhar et al. | 424/55 |
| 4,224,310 | 9/1980 | Shah | 424/54 |

FOREIGN PATENT DOCUMENTS

| | | |
|---|---|---|
| 0081674 | 8/1956 | Denmark . |
| 0079611 | 5/1983 | European Pat. Off. . |
| 0671334 | 1/1939 | Fed. Rep. of Germany . |
| 8603674 | 7/1986 | PCT Int'l Appl. . |
| 0490384 | 8/1938 | United Kingdom . |

OTHER PUBLICATIONS

*The Merck Index*, Merck and Co., Inc., Rahway, N. J., 1976, Entry Nos: 3375 and 9421.

*Primary Examiner*—F. T. Moezie
*Attorney, Agent, or Firm*—Steinberg & Raskins

[57] ABSTRACT

Tartar formation on teeth is prevented with compositions of a sodium salt ethylenediaminetetraacetic acid having a pH between about 5.5 and 9.0 in a carrier which permits application to the teeth. Aqueous solution may be used for this purpose as well as toothpaste compositions.

14 Claims, No Drawings

METHOD OF PREVENTING TARTAR FORMATION

This is a continuation, of application Ser. No. 896,801, filed Aug. 15, 1986, which is a continuation of Ser. No. 806,742 filed Dec. 9, 1985, both are now abandoned.

BACKGROUND OF THE INVENTION

Tartar is a solid, hard deposit formed on the faces of teeth. Tartar is known to provide the bacterial flora in saliva with an excellent protected environment from which some bacteria are capable of causing dental diseases such as caries and various forms of gingivitis.

In the first stage, the formation of tartar requires adherence of the so-called plaque onto the tooth face. This plaque is a porous mass consisting of organic materials, into which mass calcium and phosphate ions diffuse from the saliva and can there react to form various calcium phosphates. This results in reinforcement of the structure of the plaque which becomes hardened by the effect of crystallization of phosphates into tartar.

Due to the fact that the dental diseases mentioned are caused by the activity of certain bacteria in the surface areas of the teeth and in their recesses, the studies have been directed towards, and measures have so far been taken, almost exclusively to prevent or reduce the activity of the bacteria. This has taken place most commonly by mouth rinsing utilizing various bacteriocidal agents in the rinsing solution. Even though some additives such as chlorhexidine, have had a positive effect, the use of such agents has not been entirely satisfactory to solve the problems of decay and gingivitis.

In the last decade, fluoride-containing toothpastes and mouthwashes, and fluoridation of drinking water, have been used as means to reduce the occurrence of caries, and this has been quite efficient. However, this has not resulted in any significant reduction in the occurrence of dental diseases.

A new possibility which has been suggested has been the development of a vaccine to prevent the generation of the most detrimental of the bacteria occurring in the mouth, namely Streptococcus mutans. These experiments (described in Tiede 2000 No. 6/82, pages 17–22) are only at an early stage of development, and nothing will be known as to the effectiveness thereof for several years. In any event, this type of treatment relates to the prevention of caries resulting from only this single species of bacteria.

SUMMARY OF THE INVENTION

It is a primary object of the present invention to provide a new and different method of preventing tooth decay and gingivitis by preventing the formation of tartar.

It is another object of the present invention to provide. compositions and methods useful in preventing the formation of tartar on tooth faces, which compositions and methods have teen proved effective over long testing periods.

Other objects and advantages of the present invention will be apparent from a further reading of the specification and of the appended claims.

With the above and other objects in view, the present invention mainly comprises a composition useful for preventing formation of tartar on teeth faces, which composition comprises a sodium salt of ethylenediaminetetraacetic acid (EDTA) in a carrier which permits application to the teeth, at a pH of about 5.5–9.0. The composition may, for example, be in the form of a toothpaste or mouth rinse. The sodium salt of the EDTA at this pH has the effect of complexing calcium ions and and thus preventing the formation of phosphate nuclei essential for the formation of tartar.

As indicated above, a factor which precedes the formation of tartar is the formation of plaque on the tooth face. Plaque is formed partly of organic proteins contained in the liquid in the mouth cavity, partly "by the intermediate of polysaccharides grown by the bacteria contained in the plaque" (note Tiede 2000 above).

Due to its porous structure, the plaque can absorb different bacteria as well as valuable ions contained in the liquid in the mouth cavity, the most essential of such ions for the formation of tartar being calcium and phosphate ions. Under suitable conditions, the calcium and phosphate ions react with each other and form various calcium phosphates. In the first stage, the formation of such solid phosphate compounds requires the formation of phosphate nuclei, after which the mineralization proper of the plaque, i.e. the formation of macroscopic phosphate crystals can commence.

Consequently, mineralization of the plaque, i.e. formation of tartar, can be eliminated if it is possible to prevent the formation of phosphate nuclei and crystalline phosphate which are prerequisites for the formation of the tartar.

This idea has been proposed in Finnish Patent No. 50,054. However, as set forth therein, it was ascertained, among other things, that solutions containing EDTA are unsuitable for such purpose.

We have, however, found, as a result of long-term experiments, that the use of sodium salts of EDTA in contact with the tooth faces does give the desired effect. Initial tests were in vitro, and further tests, as will be described below, were carried out in vivo.

In accordance with the present invention it was necessary to not only provide a means for preventing the formation of tartar, but to provide conditions under which this can be achieved without damaging tooth enamel or otter parts of the oral cavity.

It has been found in accordance with the present invention that these desiderata can be achieved by compositions, such as mouth rinsing solutions, containing a sodium salt of EDTA and having a pH within the range of 5.5–9.0, preferably 6.5–8.5, more preferably about 6.7–8.0 and most preferably about 7–8.

It has been found in accordance with the present invention that the calcium-binding effect of the sodium salt of the EDTA is considerably reduced at a pH below 6.5, which is the reason that this is the preferred lower limit for the pH, while the upper limit of the pH value is determined by a value which does not cause any damage in the mouth cavity. The most desirable pH value from this standpoint, that is an entirely risk fee environment, is a pH of up to about 8.0.

The amount of the EDTA in the composition may be between about 1–20% by weight, preferably about 2–15% and most preferably about 5–7% by weight.

The use of the compositions such as the rinsing solutions of the present invention should not be started until tartar previously on the teeth has been removed. This is due to the fact that the basis of the present invention is that the calcium ions which diffused into the plaque are bound into complex form before they can react with the phosphate ions and form phosphate nuclei and a crystalline phosphate phase in the plaque.

My initial experiments to establish the effectiveness of this invention were commenced on myself by regular risings morning and evening after the dentist had thoroughly removed the tartar from my teeth. The reason for this was a particularly strong formation of tartar which had lasted for dozens of years and which had resulted in severe paradentisis. I found that for a period of three years, from 1979 to 1982, the occurrence of tartar was completely prevented. Towards the end of 1982, the rinsing were discontinued to determine whether new formation of tartar would occur. Formation of tartar was observed in about three months after which the tartar was removed and a new series of rinsing was commenced. The result was the same as earlier, namely no further occurrence of tartar.

DESCRIPTION OF PREFERRED EMBODIMENTS

On the basis of the above-described initial results, clinical experiments were carried out. In these tests, there were three test groups totaling 15 persons. Test Substances:

I: 5% Na-2-EDTA solution, pH controlled to 7.0. The solution also contained 250 ppm of NaF.

II: 5% Na-2-EDTA solution, pH controlled to 7.0.

III: Intensified cleaning method by means of tooth picks and dental floss.

Before the test was started, tartar was removed from each test person by means of an ultrasonic device, and the tooth faces were cleaned by means of a cleaning paste. Groups I and II were given instructions for the use of the test substance, and group III was taught in treatment at home. Instructions:

Groups I and II used the test solution in a quantity of about 15 ml, rinsing in the mouth morning and evening for 1 to 2 minutes, after which the mouth was rinsed with water. Group III cleaned their teeth in an intensified way by mechanical means.

Results:

Group I

Five test persons of whom four used the test substance regularly: no tartar was formed in any of these persons. With the test person who did not use the test substance regularly, formation of bacterial plaque was noticed, but no calcification of the plaque. Test period 5 weeks.

Group II

Five test persons, all of whom used the test substance regularly: no tartar was formed in any of these persons. On the contrary, two test persons had a thin bacterial plaque. Test period 4 weeks.

Group III

Five test persons who had used tooth picks and dental floss, besides brushing, for cleaning the teeth. With three test persons, it was noticed that tartar had been formed on the rear faces of the front teeth of the lower jaw. The remaining two test persons had plaque that was about to be calcified on the rear faces of the front teeth of the lower jaw. Test period 4 weeks.

The test persons in the groups had been chosen by means of a blind test method out of a test group in which, on the basis of earlier experience of treatment, tartar had always been formed within the period of time concerned. Thus, in each group there were different test persons, in respect of the formation of tartar, because saliva studies and other individual differences were not taken into account in this test.

It is well known that the presence of small quantities of fluoride in the mouth has a clear effect on the occurrence of dental caries. This effect is, however, slow, because the fluoride ion must reach an unhindered contact with the enamel face of the teeth. In practice, on the tooth faces, there is either plaque or mineralized plaque, i.e. tartar. The presence of these of course prevents the necessary efficient contact. Accordingly, it is highly advantageous to use small additions of fluoride in the mouth rinsing solution in accordance with the invention, because it is the rinsing solution that can keep the teeth from tartar. The fluoride additions may be 100 to 300 ppm, but an optimal value is about 200 to 250 ppm.

Since the EDTA agent contained in the mouth rinsing solution must reach a contact as efficient of as possible with the calcium ions contained in the plaque, penetration of the solution into the plaque must be aided as efficiently as possible. For this purpose, 0.05 to 0.17%, or 0.1 to 0.5% of sodium salt of lauroyl-sarcosine acid, which is a highly efficient and completely risk-free detergent may be added to the rinsing solution.

The compositions in accordance with the invention are not restricted to be used in the way described in the examples. A mouth rinsing solution may also consist, e.g., of a concentrate of the said compound diluted with water, or the compound may be added, e.g., to tooth paste.

The invention has been described with respect to particular compositions, it is apparent that variations and modifications can be made without departing from the spirit or the scope of the invention.

What is claimed is:

1. Method of preventing the formation of tartar on teeth, which comprises contacting teeth from which tartar has previously been removed with a sodium slat of ethylenediaminetetraaetic acid in an amount sufficient to complex with calcium ions present in the mouth about the teeth and being at a pH of about 5.5–9.0 for a time sufficient for said sodium salt of ehtylenediaminetetraaetic acid to complex any calcium ions present in the mouth about the teeth and thus prevent the formation of phosphate nuclei necessary for the formation of tartar.

2. Method according to claim 1 wherein the contact is at a pH of about 6.5–8.5.

3. The method of claim 2, wherein the contact is at a pH of about 6.7–8.

4. Method according to claim 1 wherein the contact is at a pH of about 7–8.

5. The method of claim 1, wherein the sodium salt of ethylenediaminetetraacetic acid si disodium ethylenediaminetetraacetic acid.

6. Method of claim 1, wherein said sodium salt of ethylenediaminetetraacetic acid contacts the teeth while in aqueous solution.

7. Method of claim 6, wherein the solution comprises about 1 to 20% by weight of said sodium slat of ehtylenediaminetetraaetic acid.

8. Method of claim 7, wherein the solution comprises about 2–15% by weight of said sodium salt of ethylenediaminetetraacetic acid.

9. Method of claim 8, wherein said solution comprises about 5–7% by weight of said sodium salt of ehtylenediaminetetraaetic acid.

10. Method of claim 1, wherein said sodium salt of ethylenediaminetetraacetic acid contacts the teeth while in the form of a paste.

11. Method of claim 10, wherein the paste comprises about 1 to 20% by weight of said sodium salt of ethylenediaminetetraacetic acid.

12. Method of claim 11, wherein said paste comprises about 2–15% by weight of said sodium salt of ethylenediaminetetraacetic acid.

13. Method of claim 12, wherein said paste comprises about 5–7% by weight of said sodium salt of ethylenediaminetetraacetic acid.

14. Method according to claim 1 and wherein said contact is then effected daily.

* * * * *